(12) United States Patent
Schaller

(10) Patent No.: US 10,245,036 B1
(45) Date of Patent: Apr. 2, 2019

(54) STAPLING DEVICE CLAMP AND DEPLOYMENT LOCKOUT SAFETY APPARATUS AND METHOD

(71) Applicant: AESCULAP AG, Tuttlingen (DE)

(72) Inventor: David Schaller, Redwood City, CA (US)

(73) Assignee: Aesculap AG, Tuttlingen (DE)

( * ) Notice: Subject to any disclaimer, the term of this patent is extended or adjusted under 35 U.S.C. 154(b) by 430 days.

(21) Appl. No.: 14/824,405

(22) Filed: Aug. 12, 2015

(51) Int. Cl.
*A61B 17/072* (2006.01)

(52) U.S. Cl.
CPC .............................. *A61B 17/07207* (2013.01)

(58) Field of Classification Search
CPC .................................................. A61B 17/07207
USPC ........................................................ 227/175.3
See application file for complete search history.

(56) References Cited

U.S. PATENT DOCUMENTS

| | | | | |
|---|---|---|---|---|
| 4,892,244 A * | 1/1990 | Fox | ...................... | A61B 17/068 227/120 |
| 5,397,046 A * | 3/1995 | Savage | ............ | A61B 17/07207 227/175.3 |
| 5,706,998 A * | 1/1998 | Plyley | .................. | A61B 17/072 227/175.2 |
| 5,709,334 A * | 1/1998 | Sorrentino | ....... | A61B 17/07207 227/175.2 |
| 5,715,988 A * | 2/1998 | Palmer | ............. | A61B 17/07207 227/175.3 |
| 7,886,952 B2 * | 2/2011 | Scirica | ............. | A61B 17/07207 227/175.1 |
| 2005/0023324 A1 * | 2/2005 | Doll | ................. | A61B 17/07207 227/175.2 |
| 2007/0102475 A1 * | 5/2007 | Ortiz | ................ | A61B 17/07207 227/175.2 |
| 2009/0302090 A1 * | 12/2009 | Shah | ................ | A61B 17/07207 227/180.1 |
| 2010/0065604 A1 * | 3/2010 | Weng | ............... | A61B 17/07207 227/175.2 |
| 2013/0248577 A1 * | 9/2013 | Leimbach | ........ | A61B 17/07207 227/175.2 |
| 2013/0277410 A1 * | 10/2013 | Fernandez | ........... | A61B 17/068 227/175.2 |
| 2014/0131417 A1 * | 5/2014 | Williams | ............. | A61B 17/068 227/175.3 |
| 2015/0173745 A1 * | 6/2015 | Baxter, III | ....... | A61B 17/07207 227/175.3 |
| 2015/0265275 A1 * | 9/2015 | Chen | ................ | A61B 17/07207 227/175.3 |
| 2015/0374363 A1 * | 12/2015 | Laurent, IV | ......... | A61B 17/068 227/175.3 |

(Continued)

*Primary Examiner* — Thanh K Truong
*Assistant Examiner* — Thomas M Wittenschlaeger
(74) *Attorney, Agent, or Firm* — RatnerPrestia

(57) ABSTRACT

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly comprises of a trigger member that can activate a control member to close the jaw assembly to clamp, staple, and/or cut the target tissue. The stapling device includes a safety lockout member to selective prevent the control member to close the jaw assembly to clamp, staple, and/or cut the target tissue.

12 Claims, 9 Drawing Sheets

(56) References Cited

U.S. PATENT DOCUMENTS

2016/0058447 A1\* 3/2016 Posada ................ A61B 17/105
 227/177.1
2016/0113649 A1\* 4/2016 Zergiebel ......... A61B 17/07207
 227/175.2

\* cited by examiner

STAPLING DEVICE CLAMP AND DEPLOYMENT LOCKOUT SAFETY APPARATUS AND METHOD

FIELD OF THE INVENTION

The present invention relates generally to surgical devices, and more particularly to surgical stapling or clip applying systems.

BACKGROUND

Surgical stapling devices, such as endocutters, typically staple and cut tissue to transect that tissue while leaving the cut ends of that tissue hemostatic. More advanced surgical stapling devices typically have end-effectors that are small enough in diameter so that they can be used in minimally invasive surgical procedures where access to a surgical site is obtained through a trocar, port, or small incision in the body of a patient. A typical stapling device holds a disposable single-use cartridge with several rows of staples, and includes an anvil to oppose the staples as the staples are deployed from the cartridge. During operations, the surgeon inserts the stapling device through an opening in the body (typically using a trocar), orients the end of the stapling device around the tissue to be transected, and compresses the anvil and cartridge together to clamp that tissue. Then, a row or rows of staples are deployed on either side of the transection line, and a blade is advanced along the transection line to divide the tissue.

During actuation of the endocutter, the stapling device fires all of the staples in the single-use disposable cartridge. In order to deploy more staples, the endocutter must be moved away from the surgical site and removed from within the patient. The spent cartridge is removed from the endocutter and replaced by a new cartridge. The endocutter is then reinserted into the patient for further staple deployment.

SUMMARY OF THE INVENTION

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly comprises of a trigger member that can activate a control member to close the jaw assembly to clamp, staple, and/or cut the target tissue. The stapling device includes a safety lockout member to selective prevent the control member to close the jaw assembly to clamp, staple, and/or cut the target tissue.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The jaw assembly includes an upper jaw member and a low jaw member. The stapling device includes a control member configured to operate at least one of the upper jaw member or the lower jaw member. Furthermore, the stapling device also includes a safety lockout member to selectively prevent the control member from operating at least one of the upper jaw member or the lower jaw member.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The jaw assembly includes an upper jaw member and a low jaw member. The stapling device includes a control member configured to operate at least one of the upper jaw member or the lower jaw member. Furthermore, the stapling device also includes a safety lockout member to selectively prevent the control member from operating at least one of the upper jaw member or the lower jaw member. The safety lockout member includes a first deflection element and a second deflection element selectively operated to place the safety lockout member in either an active mode or a passive mode. The active mode the safety lockout member locks out the control member from operating at least one of the upper jaw member or the lower jaw member. The passive mode the safety lockout member does not affect the operation of the control member. The first deflection element and the second deflection element may act in concert to selectively place the safety lockout member in either the active mode or the passive mode. The first deflection element may be substantially rigid. The second deflection element may be substantially flexible. The second deflection element may be a cantilevered element. The second deflection member flexes or bends in one direction in order to place the safety lockout member in the passive state.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The jaw assembly includes an upper jaw member and a low jaw member. The stapling device includes a control member configured to operate at least one of the upper jaw member or the lower jaw member. Furthermore, the stapling device also includes a safety lockout member to selectively prevent the control member from operating at least one of the upper jaw member or the lower jaw member. The safety lockout member includes a safety lockout element configured to engage with the control member. The safety lockout element prevents the control member from closing the upper jaw member or the lower jaw member.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The jaw assembly includes an upper jaw member and a low jaw member. The stapling device includes a control member configured to operate at least one of the upper jaw member or the lower jaw member. Furthermore, the stapling device also includes a safety lockout member to selectively prevent the control member from operating at least one of the upper jaw member or the lower jaw member. The stapling device includes a staple cartridge configured to engage with the safety lockout member to selectively place the safety lockout member in either an active mode or a passive mode. In the active mode, the safety lockout member locks out the control member from operating at least one of the upper jaw member or the lower jaw member. In the passive mode the safety lockout member does not affect the operation of the control member. The staple cartridge may include a deployment member configured to engage with the safety lockout member to selectively place the safety lockout member in either an active mode or a passive mode.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The jaw assembly includes an upper jaw member and a low jaw member. The stapling device includes a control member configured to operate at least one of the upper jaw member or the lower jaw member. Furthermore, the stapling device also includes a safety lockout member to selectively prevent the control member from operating at least one of the upper jaw member or the lower jaw member. Alternatively, the safety lockout member may be a one piece component. The safety lockout member may be a one piece elongate component.

BRIEF DESCRIPTION OF THE DRAWINGS

The present invention will be readily understood by the following detailed description, taken in conjunction with accompanying drawings, illustrating by way of examples of the embodiments of the invention. The figures are merely exemplary and not limiting. The objects and elements in the drawings are not necessarily drawn to scale, proportion, precise orientation or positional relationships; instead, emphasis is focused on illustrating the principles of the invention. Descriptive terms such as "upper," "lower," "upward," "downward", "forward", "backward", and the like are intended for the convenience of the reader and refer to the orientation and/or motion of parts as illustrated and described; they do not necessarily limit the orientation or operation of the features, aspects, or embodiments of the invention. The drawings illustrate the design and utility of various features, aspects, or embodiments of the present invention, in which like elements are typically referred to by like reference symbols or numerals. The drawings, however, depict the features, aspects, or embodiments of the invention, and should not be taken as limiting in their scope. With this understanding, the features, aspects, or embodiments of the invention will be described and explained with specificity and details through the use of the accompanying drawings in which.

As can be appreciated from the illustrations, the same or similar symbols or numerals are used in the different figures to indicate similar or identical items or features are being disclosed.

DETAILED DESCRIPTION

In the following detailed description, specific details are set forth in order to provide a thorough understanding of the present invention. However, it will be readily understood by those skilled in the art that the present invention may be practiced without these specific details. Alternatively, some of the well-known parts, components, hardware, methods of operations, and procedures may not be described in detail or elaborated so as to avoid obscuring the present invention; but, nevertheless, they are within the spirit and scope of the present invention.

As mentioned, surgical stapling devices, such as endocutters, typically staple and cut tissue to transect that tissue while leaving the cut ends of that tissue hemostatic. More advanced surgical stapling devices typically have end-effectors that are small enough in diameter so that they can be used in minimally invasive surgical procedures where access to a surgical site is obtained through a trocar, port, or small incision in the body of a patient. A typical stapling device holds a disposable single-use cartridge with several rows of staples, and includes an anvil to oppose the staples as the staples are deployed from the cartridge. During operations, the surgeon inserts the stapling device through an opening in the body (typically using a trocar), orients the end of the stapling device around the tissue to be transected, and compresses the anvil and cartridge together to clamp that tissue. Then, a row or rows of staples are deployed on either side of the transection line, and a blade is advanced along the transection line to divide the tissue.

As can be appreciated, it would be unsafe to deploy an empty stapling device and transect a tissue that has not been stapled or secured. Alternatively, once the staples in a staple cartridge have been deployed, it would be advantageous to prevent deployment operations with an empty staple cartridge in the stapling device. That is, it would be unsafe to deploy the knife member or cutting mechanism in the stapling device when there are no staples in the device to secure or seal the tissue that may be divided or cut by the knife member. So, at least for safety reasons, accidental deployment of the stapling device should be prevented.

Figure 1:
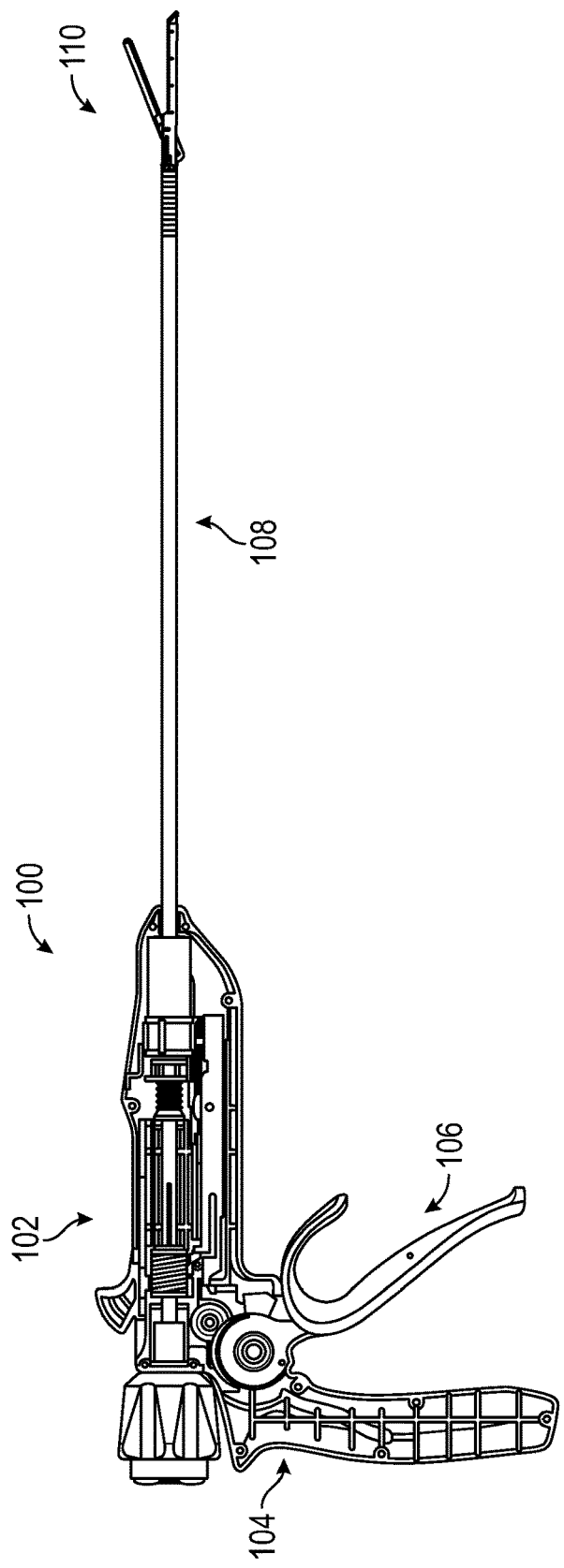
FIG. 1 illustrates an example of a surgical stapling device, in accordance with features, aspects or embodiments of the present invention.

By way of example, FIG. 1 illustrates a surgical stapling device 100 in accordance with features, aspects or embodiments of the present invention. As illustrated, the surgical stapling device 100 includes a body portion 102, a handle portion 104, a trigger member 106, a shaft member 108, and an end-effector 110.

Figure 2A:
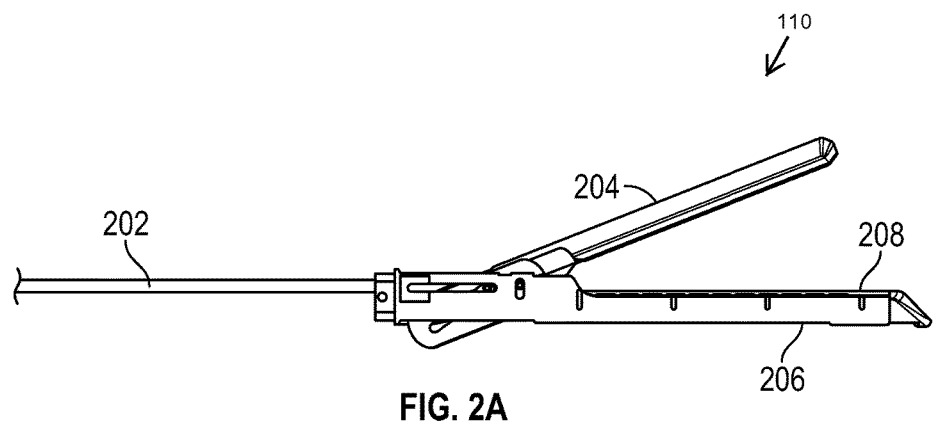
FIG. 2A and FIG. 2B illustrate a control member that is operated to control the opening and closing of the end-effector of the stapling device, in accordance with features, aspects or embodiments of the present invention.
Figure 2B:
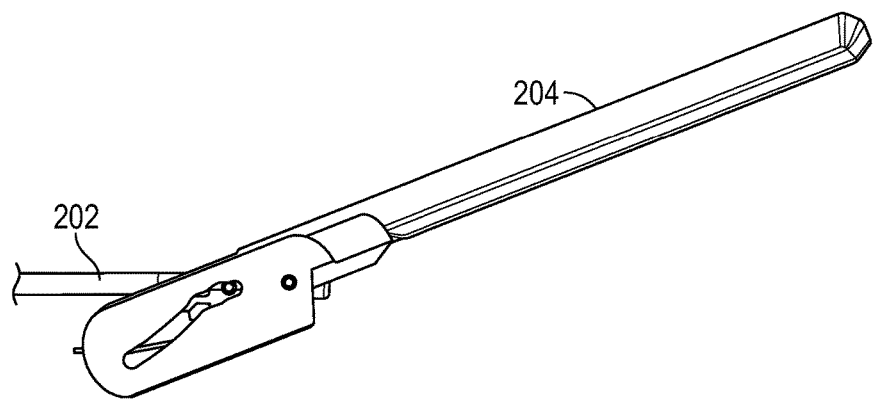

FIG. 2A and FIG. 2B illustrate a jaw control member 202 that is operated, e.g., by the trigger member 106, to control the opening and closing of jaw members 204 and 206, e.g., an anvil member 204 and a staple holder channel member 206 with a staple cartridge 208, of the end-effector 110 of the stapling device 100. In one embodiment, as illustrated in FIG. 2B, the control member 202 is operated to control the opening and closing of the anvil member 204. The control member 202 may be operated by translating or moving the control member in a forward or backward movement in order to push or pull the anvil member 204 in a closing or opening motion or position, respectively.

Figure 3:
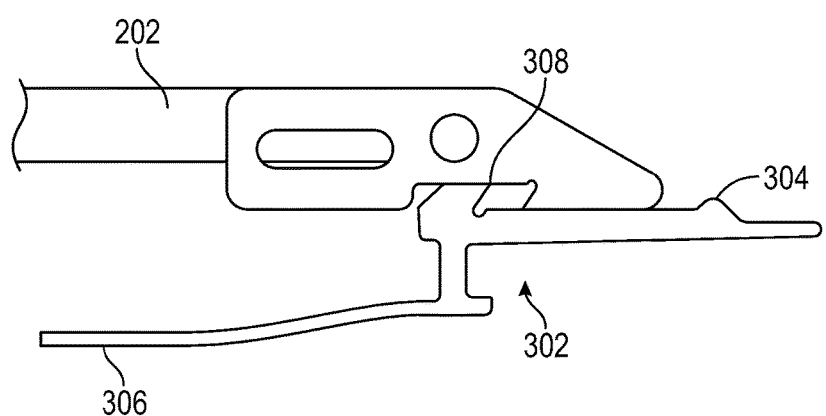
FIG. 3 illustrates the interaction of the control member with a safety lockout member of the end-effector of the stapling device, in accordance with features, aspects or embodiments of the present invention.

FIG. 3 illustrates the interaction of the jaw control member 202 with a safety lockout member 302 in accordance with an embodiment of the present invention. The lockout member 302 may include a first deflection member 304, which when activated may cause a second deflection member 306 to be activated or deflected. Typically, when the second deflection member 306 is activated or deflected, the lockout member 308 would be in a disengaged or released position to place the safety lockout member 302 in a neutral or lockout released configuration.

Figure 4:
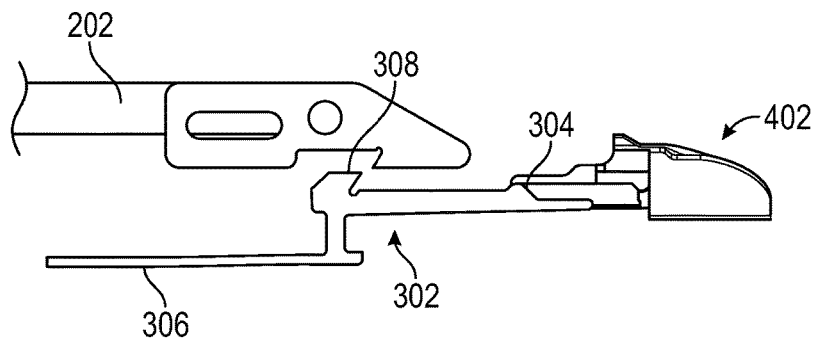
FIG. 4 illustrates the interaction of the safety lockout member with the control member and a staple deployment member, in accordance with features, aspects or embodiments of the present invention.

FIG. 4 illustrates the interaction of the safety lockout member 302 with the control member 202 and a staple deployment member 402. As illustrated, the staple deployment member 402 engages with the first deflection member 304. The engagement of the staple deployment member 402 may cause the second deflection member 306 to be activated or deflected, which would place the safety lockout member 302 in a neutral or lockout released configuration.

Figure 5:
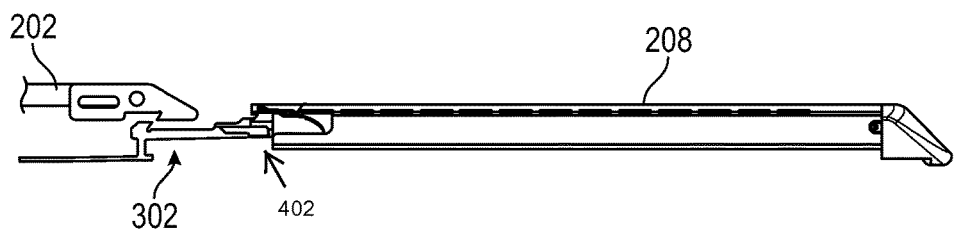
FIG. 5 illustrates a perspective view of the safety lockout member with the control member and the staple deployment member in relation with a staple cartridge, in accordance with features, aspects or embodiments of the present invention.

FIG. 5 illustrates a perspective view of the safety lockout member 302 with the jaw control member 202 and the staple deployment member 402 in relation with a staple cartridge 208 in accordance with one embodiment of the present invention.

Figure 6A:
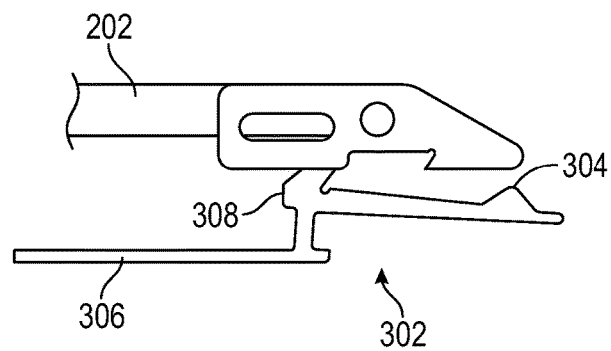
FIG. 6A and FIG. 6B illustrate one phase of interaction of the control member with the safety lockout member and the end-effector of the stapling device, such as jaws in an open configuration with no staple cartridge loaded, in accordance with features, aspects or embodiments of the present invention.
Figure 6B:
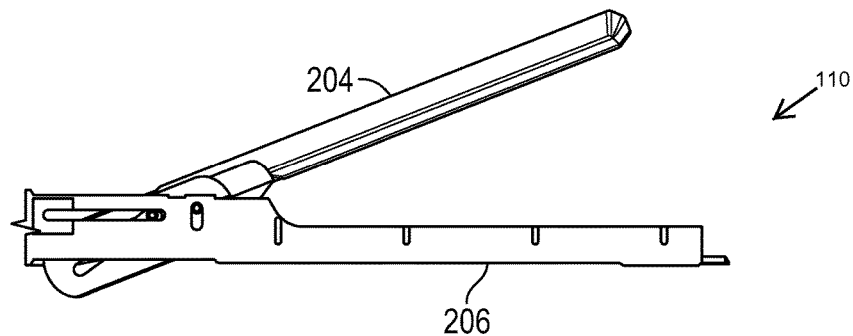

FIG. 6A and FIG. 6B illustrate one phase of interaction of the control member 202 with the safety lockout member 302 and the end-effector 110 of a stapling device 100 in accordance one embodiment of the present invention. For example, in FIG. 6A, the control member 202 may be advanced 'forward' to place the anvil member 204 in an open position, as illustrated in FIG. 6B. Also, illustrated in FIG. 6A, as the control member 202 is advanced forward, a portion of the control member 202 rides over the lockout member or lockout element 308. Also as can be appreciated from the illustration of FIG. 6A, the second deflection member 306 is activated to allow the safety lockout member 302 to flex or bend, such that the control member 202 can ride over the lockout member or locking element 308.

Figure 7A:
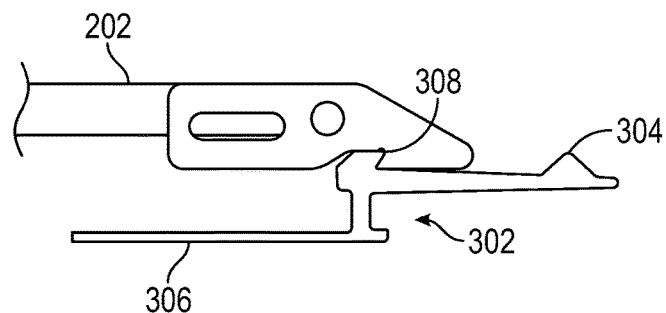
FIG. 7A and FIG. 7B illustrate another phase of interaction of the control member with the safety lockout member and the end-effector of the stapling device, such as jaws in a locked out configuration with no staple cartridge loaded, in accordance with features, aspects or embodiments of the present invention.
Figure 7B:
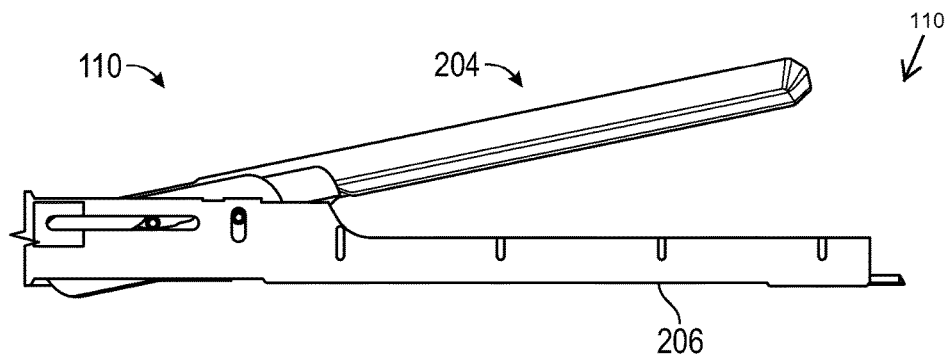

FIG. 7A and FIG. 7B illustrate another phase of interaction between the control member 202 and the safety lockout member 302 and the resulting configuration of the end-effector 110 of the stapling device 100. As may be noted, in FIG. 7B, a staple cartridge 208 is not loaded into or onto the staple holder channel member 206 of the end-effector 110. Accordingly, nothing has engaged the first deflection member 304 and it is in a substantially unengaged or neutral state. In this unengaged or neutral state, when the control member 202 is retracted backward or proximally, e.g., to close the anvil member 204, the lockout member or locking element 308 engages with the control member 202 locking or preventing the control member 202 from being retracted. FIGS. 6A and 6B along with FIG. 7A and FIG. 7B provide clear illustration of the operation as described. FIG. 6A illustrates the interaction between the control member 202 prior to being retracted, prior to engaging the locking member 308, and prior to being "locked out" by the locking element 308 of the safety lockout member 302. FIG. 6B illustrates the associated position of the anvil member 204, e.g., in a substantially opened position. Meanwhile, FIG. 7A illustrates the control member 202 being retracted (such as from a prior position as illustrated in FIG. 6A) and being engaged by the locking element 308, and FIG. 7B illustrates the associated position of the anvil member 204, e.g., in a partially closed position. By the way, "lock-out" is a term of art used in the safety industry to describe a condition in which a hazardous condition is controlled by using a safety mechanism to prevent a hazardous condition from occurring by "locking out" and "tagging out" a hazardous condition trigger.

Figure 8A:
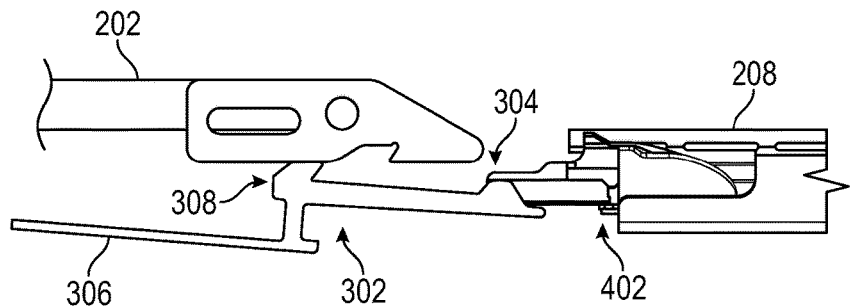
FIG. 8A and FIG. 8B illustrate a further phase of interaction of the control member with the safety lockout member and the end-effector of the stapling device, such as jaws in an open configuration with staple cartridge loaded, in accordance with features, aspects or embodiments of the present invention.
Figure 8B:
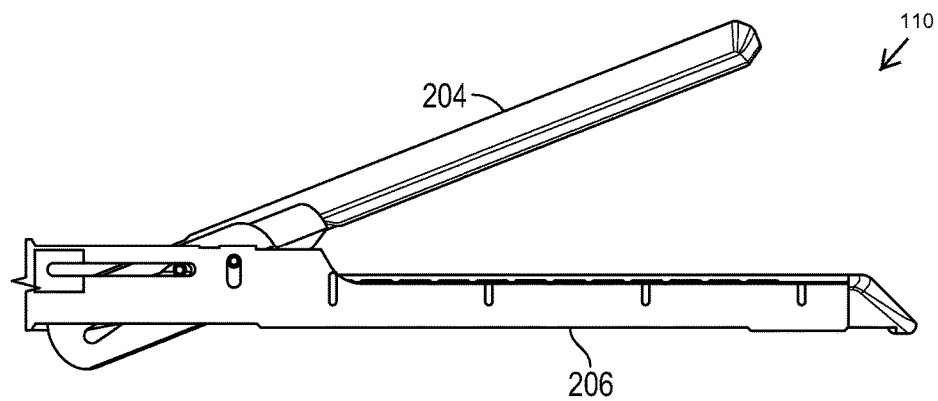

FIG. 8A and FIG. 8B illustrate a further phase of interaction between the control member 202, the safety lockout member 302, and a staple cartridge 208 that is loaded onto or into the staple holder channel 206 (not shown for purpose of clarity) of a stapling device 100 (also not shown). For example, with the jaws of the end-effector 110 in an open configuration, as illustrated in FIG. 8B, a staple cartridge 208 is loaded onto or into the staple holder channel 206. The staple cartridge 208 engages with the first deflection member 308 put the safety lockout member 302 in a passive state, which allows the control member 202 to be fully operational, e.g., fully advanced or fully retracted, as illustrated in FIG. 8A. In addition, the second deflection member 306 is also activated to allow the safety lockout member 302 to be put into a passive state. The deflection member 306 may possess substantial spring properties that allow deflection member to deflect, bend, move, etc. The first deflection member 304 and the second deflection member 306 may work substantially in concert such that the safety lockout member 306 can be placed in a passive state, e.g., to allow the control member 202 to be fully operational, or in active state, e.g., to prevent the control member 202 or the stapling device to be fully operational—in a lockout or locked-out condition. As can be appreciated, with the safety lockout member 302, the stapling device 100 cannot be fully operational unless a staple cartridge 208 has been loaded onto or into the stapling device 100. This is a desirable condition, because it would be unsafe to have the stapling device to be able to be fully operational without a staple cartridge (with undeployed staples) loaded onto or into the stapling device. An empty unloaded stapling device that is fully operational can cut tissue without the ability to seal or secure the cut tissue—such a condition is absolutely undesirable and creates an unsafe condition for a patient. Hence, the safety lockout device 302 is developed to prevent such undesirable and unsafe condition.

Figure 9A:
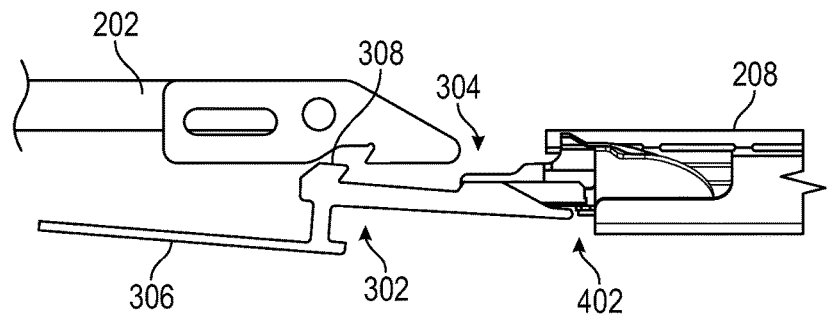
FIG. 9A and FIG. 9B illustrate yet another phase of interaction of the control member with the safety lockout member and the end-effector of the stapling device, such as jaws in trocar entry configuration with staple cartridge loaded, in accordance with features, aspects or embodiments of the present invention.
Figure 9B:
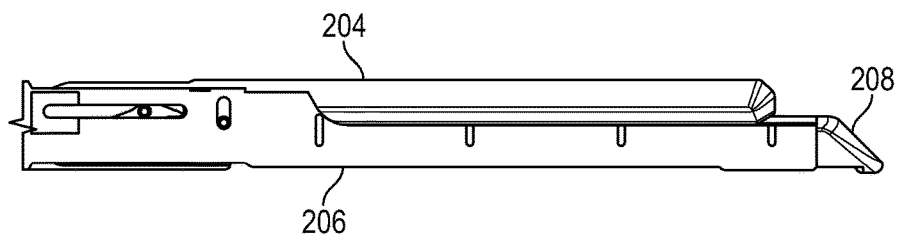

FIG. 9A and FIG. 9B illustrate yet another phase of interaction between the jaw control member 202 with the safety lockout member 302 and the end-effector 110 of the stapling device 100. As can be appreciated from FIG. 9A and FIG. 9B, a staple cartridge 208 is loaded onto or into the end-effector 110, which places the safety lockout member 302 in a passive or neutral state that allows full operation of the jaw control member 202. In other words, the lockout feature of the safety lockout member 302 is placed in a passive or neutral state so that it does not lockout the control member from full deployment operations, e.g., deploying staples and deploying a knife or cutting member of the stapling device. It would be undesirable to be able to deploy a knife or cutting member of a stapling device when no staple cartridge is present or an empty staple cartridge is present. To be more clear, the staple deployment member 402 of a staple cartridge 208 engages with the safety lockout member 302 and places the safety lockout member 302 in a passive or neutral state to allow fully operation of the jaw control member 202. If the staples in a staple cartridge are already deployed by the deployment member 402, then the deployment member 402 would not be in a position to engage the safety lockout member 302 to put it in a passive or neutral state. As FIG. 9A illustrates, the jaw control member 202 is being advanced forward, which places one or more of the jaw members 204 and 206 (e.g., the anvil 204 and the staple holder channel 206 with the staple cartridge 208) in a trocar entry configuration, as illustrated in FIG. 9B.

Figure 10A:
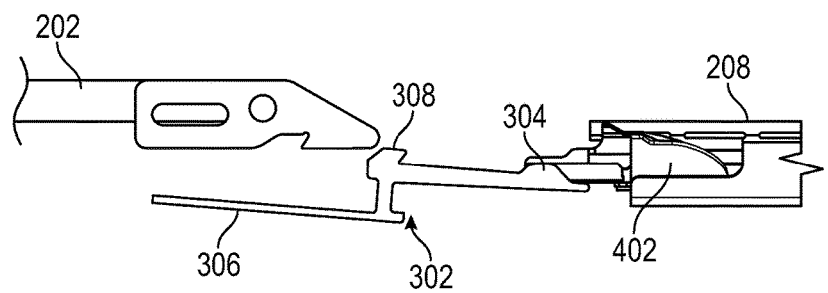
FIG. 10A and FIG. 10B illustrate another phase of interaction of the control member with the safety lockout member and the end-effector of the stapling device, such as jaws in a clamped configuration with staple cartridge loaded, in accordance with features, aspects or embodiments of the present invention.
Figure 10B:
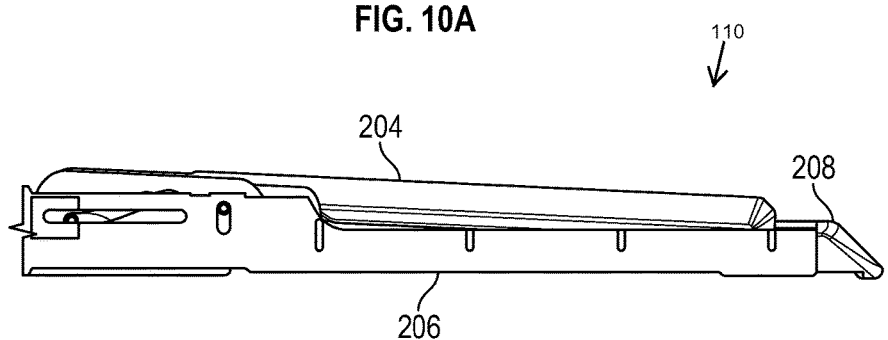

FIG. 10A and FIG. 10B illustrate another phase of interaction between the jaw control member 202 and the deployment safety lockout member 302 along with the end-effector of the stapling device 100. As illustrated in FIG. 10A, the deployment member 402 engages with the deployment safety lockout member 302, which puts the safety lockout member 302 in a passive or neutral state. The jaw control member 202 is further retracted, as illustrated in FIG. 10A, to further closes at least one or more of the jaw members 204 and/or 206 of the end-effector 110, as illustrated in FIG. 10B. The further closing of at least one of the jaw members, e.g., the anvil member 204, may place the jaw members 204 and 260 in a tissue clamp configuration.

Figure 11A:
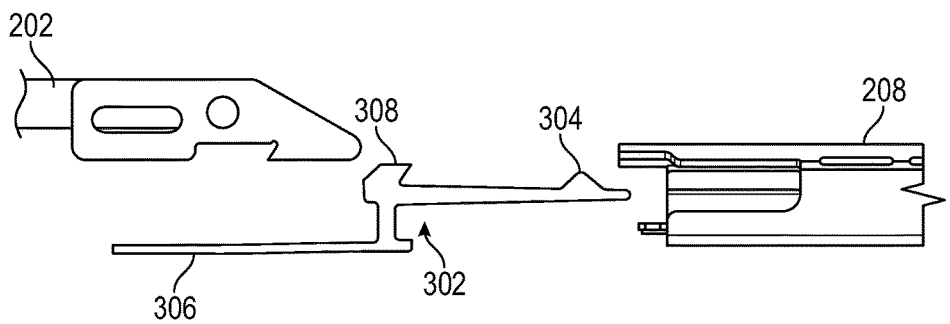
FIG. 11A and FIG. 11B illustrate a further phase of interaction of the control member with the safety lockout member and the end-effector of the stapling device, such as jaws in a clamped configuration with staples deployed in the staple cartridge, in accordance with features, aspects or embodiments of the present invention.
Figure 11B:
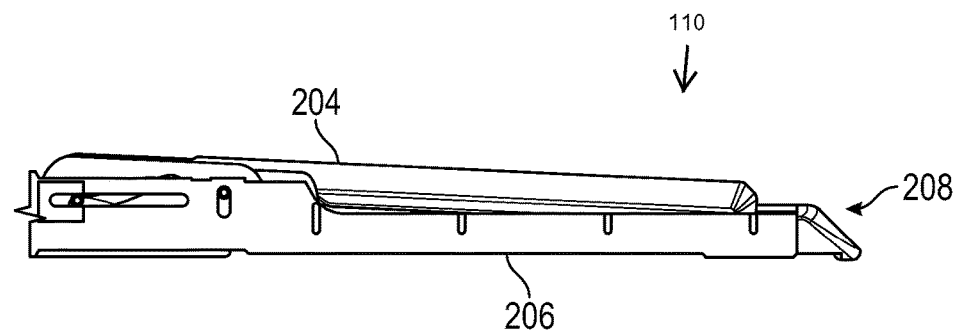

FIG. 11A and FIG. 11B illustrate a further phase of interaction of the jaw control member 202 with the deployment safety lockout member 302 and the end-effector 110 of the stapling device 100 after the staples in the staple cartridge 202 have been deployed by the deployment member 402. As illustrated in FIG. 11A, since the deployment member 402 has been activated to deploy staples in the staple cartridge 208, its position has changed and it no longer engages with the safety lockout member 302. Also illustrated in FIG. 11A, the control member 202 has been substantially retracted, and the retraction of the control member 202 has substantially pulled at least one of the jaws members (e.g., anvil member 204 or staple holder channel member 206) shut or in a clamped configuration.

Figure 12A:
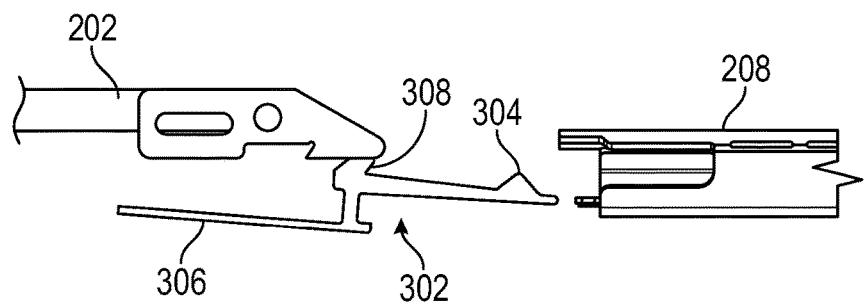
FIG. 12A, FIG. 12B, and FIG. 12C illustrate yet another phase of interaction of the control member with the safety lockout member and the end-effector of the stapling device, such as jaws in an unclamped configuration with staples deployed in the staple cartridge, in accordance with features, aspects or embodiments of the present invention.
Figure 12B:
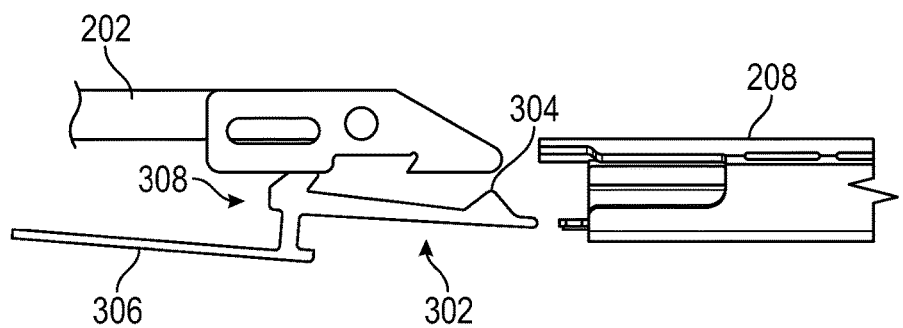
Figure 12C:
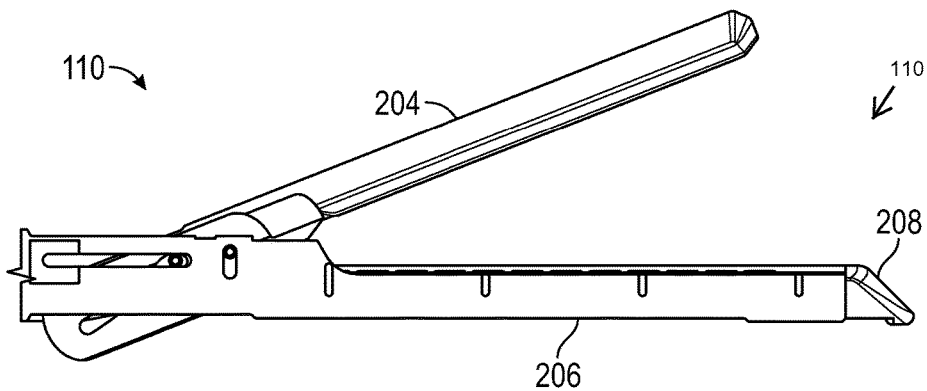

FIG. 12A, FIG. 12B, and FIG. 12C illustrate yet another phase of interaction of the control member 202 with the safety lockout member 302 and the end-effector 110 of the stapling device 100. For example, FIG. 12A and FIG. 12B illustrate that the control member 202 is being advanced to open at least one of the jaw members 204 or 206 in order to place the in an unclamped configuration. As illustrated in this example, the staples in the staple cartridge have been deployed, the jaw members are placed in an unclamp position in order to release the clamped tissue after deployment of the staples in the staple cartridge 208.

Figure 13A:
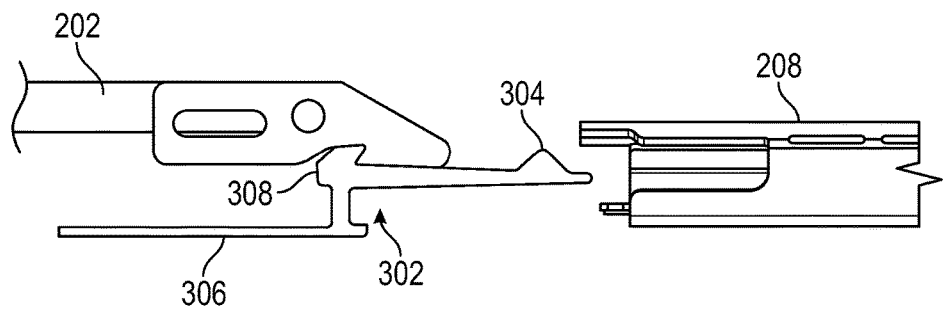
FIG. 13A and FIG. 13B illustrate yet another phase of interaction of the control member with the safety lockout member and the end-effector of the stapling device, such as jaws in a trocar exit configuration with staples deployed in the staple cartridge, in accordance with features, aspects or embodiments of the present invention.
Figure 13B:
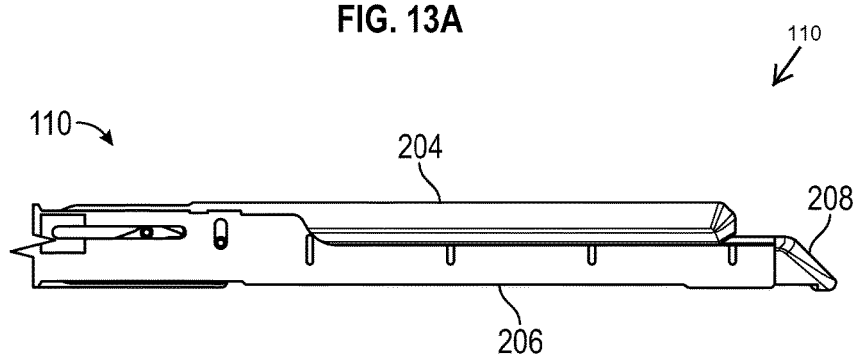

FIG. 13A and FIG. 13B illustrate yet another phase of interaction of the control member 202 with the safety lockout member 302 and the end-effector 110 of the stapling device. As illustrated in FIG. 13A, the control member 202 is retracted to pull at least one of the jaw members 204 and/or 26 to a substantially closed position or trocar exit configuration. Since the deployment member 402 has been activated to deploy staples in the staple cartridge 208, it is no longer in position to engage with the safety lockout member 302. As such, the safety lockout member 302 is in an active state, and as illustrated in FIG. 13A, the safety lockout member 302 prevents the control member 202 from being further retracted, such as placing the jaw member 204 and 206 in a tissue clamp mode or configuration, as illustrated in FIG. 13B.

Figure 14:
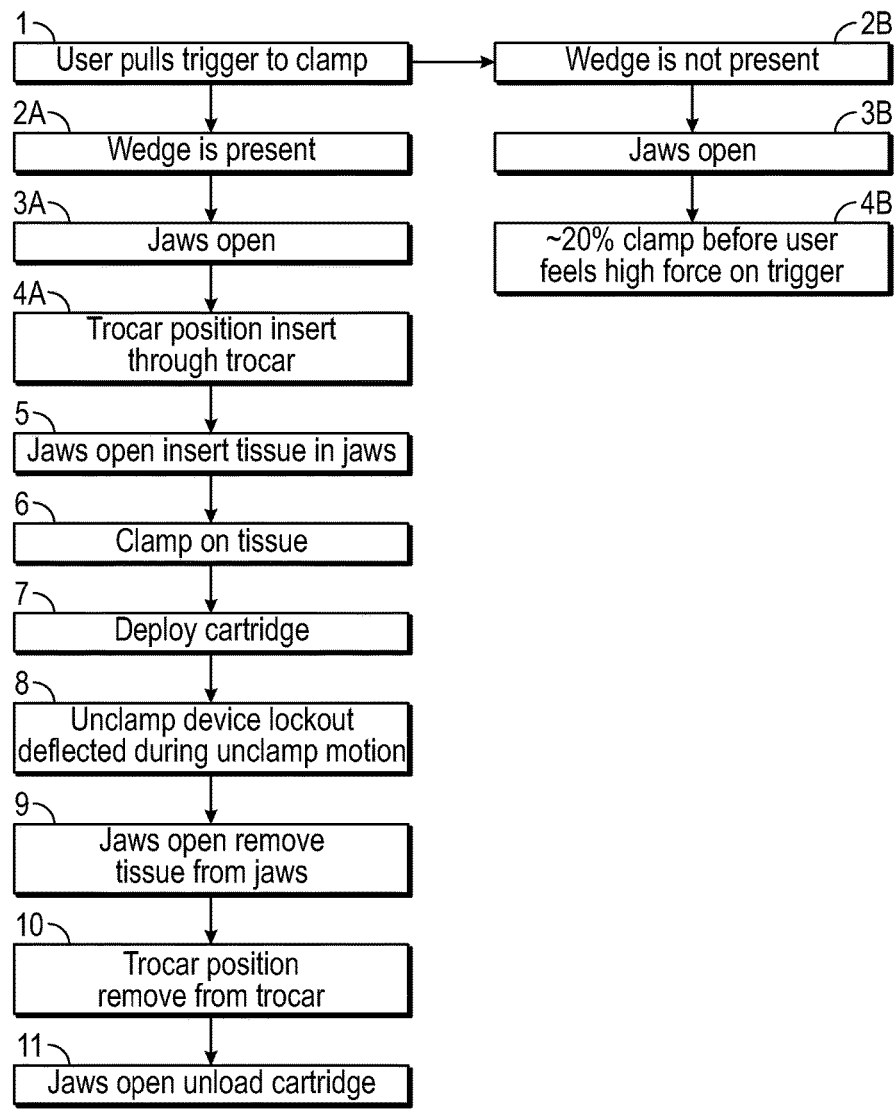
FIG. 14 illustrates a flowchart of operational process with the safety lockout member implemented in the end-effector of the stapling device, in accordance with features, aspects or embodiments of the present invention.

FIG. 14 illustrates a flowchart of operational process steps of a stapling device 100 with a safety lockout member 302 to prevent inadvertent activation of the stapling device, e.g., cutting of tissue without staples loaded onto or into the stapling device. As illustrated in FIG. 14, the operational process starts an initial trigger activation to begin clamping cycle, in Step 1. In the initial step, the jaw members 204 and 206 are typically open for loading of the staple cartridge 208 onto or into one of the jaw members. If the staple cartridge 208 has been loaded onto or into one of the jaw members, e.g., staple holder channel member 206, then the deployment member 402 would engage with the safety lockout member 302 and put it into a passive or neutral state, Steps 2A and 3A. The initial activation of the trigger member 106 will place the jaw members 204 and 206 into a trocar entry mode or configuration, in Step 4A. Alternatively, if a staple cartridge 208 is not loaded onto or into the stapling device 100 or a spent staple cartridge 208 has not been replaced, then either no deployment member 402 or the deployment member 402 is not in the appropriate position to place the safety lockout member 302 in a passive or neutral state, Step 2B. The initial activation of the trigger member 106 will cause the control member 202 to encounter the safety lockout member 302 and the control member 202 would locked-out from closing the jaw members to close the jaw members. Hence the jaw members would remain open, Step 3B. Typically, the user, e.g., the surgeon performing the operation, would feel high force on the trigger and realize the operation should be stopped or aborted, in Step 4B. Once the end-effector 110 of the stapling device has passed through the trocar, the trigger member is activated to open at least one of the jaw members, e.g., anvil member 204 or staple holder member 208, to find and clamp a target tissue for performing the surgical procedure, in Step 5. Upon finding the target tissue, the tissue is clamped between the jaw members 204 and 206, in Step 6. When ready, staples are deployed from the staple cartridge 208, in Step 7. Typically, the stapled tissue is then transected by a cutting member in the stapling device to separate the stapled tissue. The stapling device is opened, unclamps and releases the stapled tissue, in Step 8 and Step 9. During operation of this step, the safety lockout member 302 is deflected by the control member 202 as it is moved or retracted to unclamp the jaw members. Once again the end-effector 110 is placed in a trocar mode or configuration, so that the end-effector 110 can be withdrawn through the trocar and out of the surgical cavity of the patient, in Step 10. Finally, the jaw members are opened to unload the used or spent staple cartridge 208, in Step 11. A new staple cartridge may be loaded and the process steps of using the stapling device 100 can be repeated.

Multiple features, aspects, and embodiments of the invention have been disclosed and described herein. Many combinations and permutations of the disclosed invention may be useful in anastomosis surgical procedures, and the invention may be configured to support various grafting procedures. One of ordinary skill in the art having the benefit of this disclosure would appreciate that the foregoing illustrated and described features, aspects, and embodiments of the invention may be modified or altered, and it should be understood that the invention generally, as well as the specific features, aspects, and embodiments described herein, are not limited to the particular forms or methods disclosed, but also cover all modifications, equivalents and alternatives. Further, the various features and aspects of the illustrated embodiments may be incorporated into other embodiments, even if not so described herein, as will be apparent to those ordinary skilled in the art having the benefit of this disclosure.

Although particular features, aspects, and embodiments of the present invention have been shown and described, it should be understood that the above discussion is not intended to limit the present invention to these features, aspects, and embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention.

What is claimed:

1. A stapling device, comprising:
   an end-effector with an upper jaw member and a lower jaw member;
   a control member to operate at least one of the upper jaw member and the lower jaw member;
   a safety lockout member to selectively prevent the control member from operating at least one of the upper jaw member or the lower jaw member; and
   a cutting member that is movable along a transection line to divide tissue,
   the control member being selectively movable over the safety lockout member to a forward position to place the at least one of the upper jaw member and the lower jaw member in an open position,
   the control member also being selectively movable over the safety lockout member to a retracted position to place the at least one of the upper jaw member and the lower jaw member in a fully closed position,
   the safety lockout member being movable to a passive mode, in which the safety lockout member permits the control member to ride over the safety lockout member and into the retracted position to place the at least one of the upper jaw member and the lower jaw member in the fully closed position, and
   the safety lockout member being movable to an active mode, in which the safety lockout member engages with the control member to prevent the control member from riding over the safety lockout member and into the retracted position, preventing the at least one of the upper jaw member and the lower jaw member from being placed in the fully closed position.

2. The stapling device of claim 1, wherein the safety lockout member includes a first deflection element and a second deflection element selectively operated to place the safety lockout member in either the active mode or the passive mode,
   wherein in the active mode the safety lockout member locks out the control member from operating at least one of the upper jaw member or the lower jaw member,
   wherein in the passive mode the safety lockout member does not affect the operation of the control member.

3. The stapling device of claim 2, wherein the first deflection element and the second deflection element act in concert to selectively place the safety lockout member in either the active mode or the passive mode.

4. The stapling device of claim 2, wherein the first deflection element is substantially rigid.

5. The stapling device of claim 2, wherein the second deflection element is substantially flexible.

6. The stapling device of claim 2, wherein the second deflection element is a cantilevered element.

7. The stapling device of claim 5, wherein the second deflection member flexes or bends in one direction in order to place the safety lockout member in the passive mode.

8. The stapling device of claim 1, wherein the safety lockout member includes a safety lockout element configured to engage with the control member,
   wherein the safety lockout element prevents the control member from closing the upper jaw member or the lower jaw member.

9. The stapling device of claim 1 further comprising a staple cartridge configured to engage with the safety lockout member to selectively place the safety lockout member in either an active mode or a passive mode,
   wherein in the active mode the safety lockout member locks out the control member from operating at least one of the upper jaw member or the lower jaw member,
   wherein in the passive mode the safety lockout member does not affect the operation of the control member.

10. The stapling device of claim 9, wherein the staple cartridge includes a deployment member configured to engage with the safety lockout member to selectively place the safety lockout member in either the active mode or the passive mode.

11. The stapling device of claim 1, wherein the safety lockout member is a one piece component.

12. The stapling device of claim 1, wherein the safety lockout member is a one piece elongate component.

* * * * *